US006403093B1

(12) United States Patent
Persing et al.

(10) Patent No.: US 6,403,093 B1
(45) Date of Patent: *Jun. 11, 2002

(54) METHODS TO DETECT GRANULOCYTIC EHRLICHIOSIS

(75) Inventors: David H. Persing; Elizabeth S. Bruinsma, both of Rochester, MN (US)

(73) Assignee: Mayo Foundation for Medical Education and Research, Rochester, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/828,199

(22) Filed: Mar. 21, 1997

(51) Int. Cl.$^7$ .................. A61K 39/02; A61K 39/108; A61K 39/00; C07K 1/00
(52) U.S. Cl. ................ 424/184.1; 424/185.1; 424/190.1; 424/136.1; 424/191.1; 424/192.1; 424/234.1; 424/241.1; 530/300; 530/350; 530/380; 530/387.1; 530/388.4; 530/388.7; 530/827; 435/69.1; 435/69.3
(58) Field of Search ................ 424/184.1, 185.1, 424/130.1, 234.1, 192.1, 241.1, 191.1; 530/300, 350, 380, 387.1, 388.6, 388.7, 827; 435/69.1, 69.3

(56) References Cited

U.S. PATENT DOCUMENTS 4,879,213 A * 11/1989 Fox et al.

FOREIGN PATENT DOCUMENTS

WO      9639484    * 12/1996

OTHER PUBLICATIONS

Burgets et al. J. Cell. Biol. 1992 vol. 111, 2129–2138.*
Lazar et al Mol. & Cell Biol. 1988 vol. 8, No. 3, 1247–1252.*
Asanovich, K.M., et al., "Partial charaterization of cloned genes encoding immunoreactive proteins of *Ehrlichia equi* and the agent of human granulocytic Ehrlichiosis (HGE)", Abstracts of the General Meeting of the American Society for Microbiology, May 19, 1996, 22 XP002058855, Abstract D–22.
Kolbert, C.P., et al., "Characterization of an Immunoreactive Protein from the agent of Human Granulocytic Ehrlichiosis", *Journal of Clinical Microbiology*, pp. 1172–1178, (May 1997).
Kolbert, C.P., et al., "Evidence for Human Granulocytic Ehrlichiosis in patients with suspected Lyme disease", 95th General Meeting of the American Society for Microbilogy, Washing USA, vol. 95, p. 36, (May 21–25, 1998).

Yu, X., et al., "Cloning and sequencing of the gene for a 120–kDa immunodominant protein of *Ehrlichia chaffeensis*", *Gene*, vol. 184, pp. 149–154, (1997).

Sumner, J.W., et al., "*Ehrlichia chaffeensis* expresses an Immunoreactive Protein Homologous to the *Escherichia coli* GroEL protein", *Infection and Immunity*, pp. 3536–3539, (Aug. 1993).

Bakken, J.S., et al., "Clinical and Laboratory Characteristics of Human Granulocytic Ehrlichiosis", *JAMA*, 275, 199–205, (Jan., 1996).

Bakken, J.S., et al., "Human Granulocytic Ehrlichiosis in the Upper Midwest United States", *JAMA*, 272, 212–218, (Jul., 1994).

Chen, S.–M., et al., "Identification of a Granulocytotropic Ehrlichia Species as the Etiologic Agent of Human Disease", *Journal of Clinical Microbiology*, 32, 589–595, (Mar., 1994).

Dumler, J.S., et al., "Serologic Cross–Reactions Among *Ehrlichia equi*, *Ehrlichia phagocytophila*, and Human Granulocytic Ehrlichia", *Journal of Clinical Microbiology*, 33, 1098–1103, (May, 1995).

Goodman, J.L., et al., "Direct Cultivation of the Causative Agent of Human Granulocytic Ehrlichiosis", *The New England Journal of Medicine*, 334, 209–215, (Jan., 1996).

Kolbert, C., "Detection of the Agent of Human Granulocytic Ehrlichiosis by PCR", In: *PCR Protocols for Emerging Infectious Diseases (A Supplement to Diagnostic Molecular Microbiology: Principles and Applications)*, D. H. Persing (ed.), ASM Press, Washington, D.C., pp. 106–111, (1993).

Pancholi, P., et al., "*Ixodes dammini* as a Potential Vector of Human Granulocytic Ehrlichiosis", *The Journal of Infectious Diseases*, 172, 1007–1012, (Oct., 1995).

Relman, D.A., et al., "Genotypic Methods for Microbial Identification", In: *PCR Protocols for Emerging Infectious Diseases (A Supplement to Diagnostic Molecular Biology: Principles and Applications)*, D.H. Persing (ed.), ASM Press, Washington, D.C., pp. 3–31, (1993).

(List continued on next page.)

*Primary Examiner*—Lynette R. F. Smith
*Assistant Examiner*—Padma Baskar
(74) *Attorney, Agent, or Firm*—Schwegman, Lundberg, Woessner & Kluth, P.A.

(57) ABSTRACT

An isolated nucleic acid molecule associated with human granulocytic ehrlichiosis is provided. Also provided are methods to detect the presence of the nucleic acid molecule, and antibodies specific for the polypeptide encoded by the nucleic acid molecule, in a sample derived from a mammal.

4 Claims, 8 Drawing Sheets

OTHER PUBLICATIONS

Figure 3A:
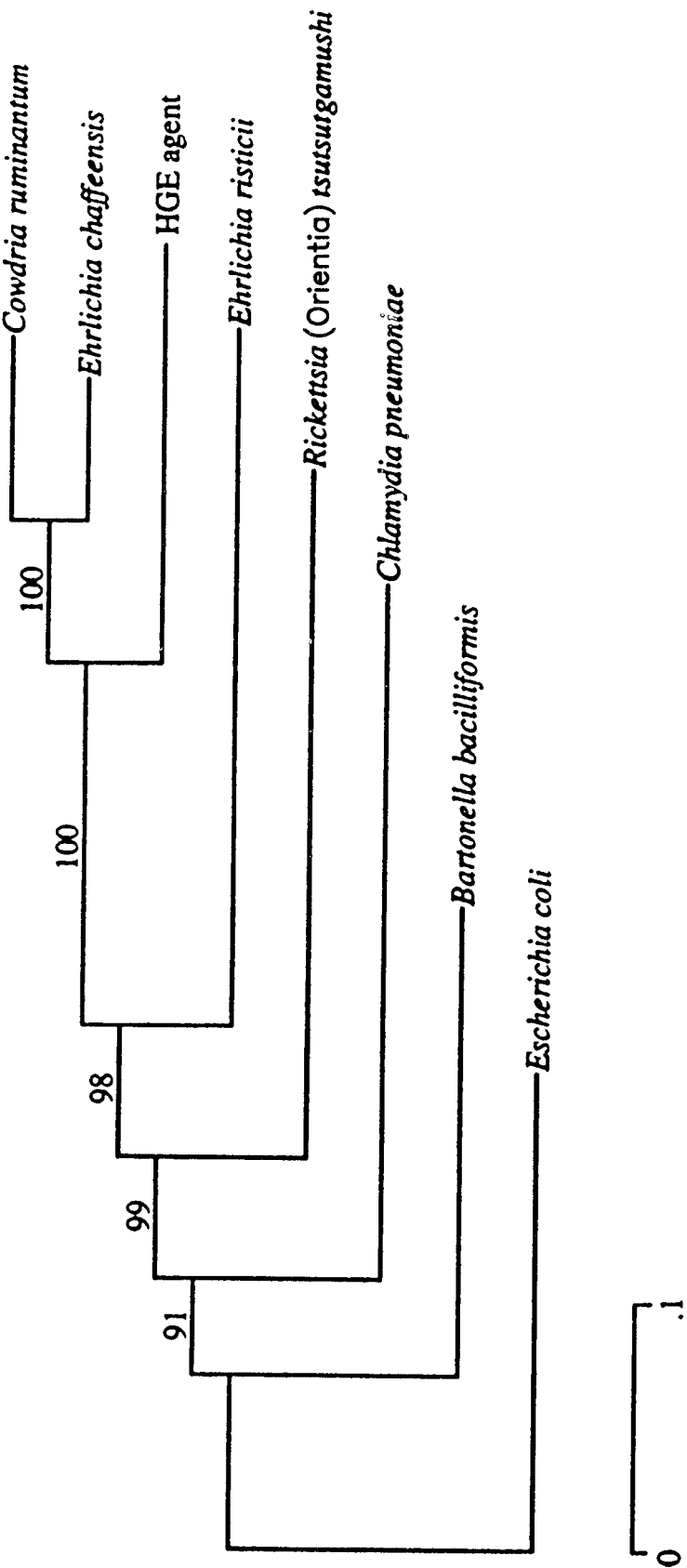

Telford III, S.R., et al., "Perpetuation of the Agent of Human Granulocytic Ehrlichiosis in a Deer Tick–Rodent Cycle", *Proc. Natl. Acad. Sci. USA*, 93, 6209–6214, (Jun., 1996).

Versalovic, J., et al., "Nucleic Acid Sequencing Studies of Microbial Pathogens: Insights into Epidemiology, Virulence, Drug Resistance, and Diversity", *In: PCR Protocols for Emerging Infectious Diseases (A Supplement to Diagnostic Molecular Microbiology: Principles and Applications)*, D. H. Persing (ed.), ASM Press, Washington, D.C., pp. 59–88, (1993).

Warner, C.K., et al., "Genus–and Species–Level Identification of Ehrlichia Species by PCR and Sequencing", *In: PCR Protocols for Emerging Infectious Diseases (A Supplement to Diagnostic Molecular Microbiology: Principles and Applications)*, D. H. Persing (ed.), ASM Press, Washington, D. C., pp. 100–105, (1993).

* cited by examiner

```
   1 CAGTGGGCTG GTAATGAAAT AGAGTTCGAC GGTAAGAAGT TCATAGTGAT
  51 GAAGGAGAGT GACATAATAG CTAAGGAAGC ATAGTCTTAT GCTACGGTTG
 101 TTTGTTCTAT TGGTCTAAAG TTTAGGAGGT TCAAAAATGT CAAATACGGT
 151 AGTCACGGGT GAGGTATTAG ATAAGTCTAT TAGGGAGGTA GTACGCATCC
 201 TAGAAGATGC AGTTGGTTGT ACTGCTGGTC CTAAAGGCCT CACTGTAGCG
 251 ATTAGTAAGC CTTATGGGTC GCCAGAGATC ACAAAGGATG GCTACAAGGT
 301 AATGAAGAGT ATAAAGCCTG AAGAACCACT GGCTGCCGCT ATAGCGAGCA
 351 TCATTACTCA GAGTGCTTCT CAGTGTAATG ATAAGGTGGG AGATGGAACT
 401 ACTACATGCT CCATACTAAC GGCAAAAGTG ATTGAAGAAG TCTCAAAAGC
 451 GAAAGCTGCT GGATCTGATA TTGTTAGCAT AAAGAATGGT ATTCTCAAGG
 501 CTAAGGAAGC GGTTCTTACA GCGCTTATGT CTATGAGACG TGAAGTAGAA
 551 GAAGACGAAA TTGCACAAGT TGCAACATTG TCTGCGAATG GAGACAAGAA
 601 CATAGGAAGT AAGATTGCAC AGTGTGTTAA AGAAGTCGGT AAAGACGGTG
 651 TTATAACTGT TGAAGAAAGC AAAGGCTTCA GGATCTAGA AGTTGAAAAG
 701 ACTGATGGTA TGCAGTTTGA TCGCGGATAT CTTTCGCCTT ACTTTGTTAC
 751 AAATGCTGAA AAAATGCTGG TGGAATTTGA AAATCCATAC ATATTCCTTA
 801 CTGAAAAGAA GATTAATCTT GTACAAAGCA TTCTACCAAT CTTAGAAAAC
 851 GTTGCACGGT CTGGAAGACC ATTGCTCATC ATAGCTGAAG ACGTTGAAGG
 901 TGAAGCTCTG AGCACGCTTG TACTCAATAA GCTCCGTGGT GGCCTTCAAG
 951 TTGCTGCTGT AAAGGCGCCT GGTTTCGGTG ACAGAAGAAA AGACATGCTT
1001 GGCGATATTG CTGTAATAGT AGGCGCTAAG TATGTAGTAA ATGACGAGCT
1051 TGCTGTTAAG ATGGAAGACA TCGCTCTAAG CGATCTTGGT ACTGCTAAGA
```

FIG. 1A

```
1101 GCGTGCGAAT CACAAAAGAC GCAACTACTA TTATAGGTAG TGTTGATAGC
1151 AGTTCTGAAA GCATAGCTAG CAGGACTAAT CAAATCAAAG CTCAGATAGA
1201 AAATTCTAGT TCTGATTATG ACAAGGAAAA GCTTAGAGAA CGTTTAGCGA
1251 AGCTTTCCGG TGGCGTTGCT GTACTCAAGG TTGGTGGATC CAGCGAAGTT
1301 GAGGTGAAGG AACGCAAAGA CAGAGTAGAA GATGCTTTAC ATGCTACTAG
1351 AGCTGCTGTT GAGGAAGGTG TAGTACCTGG TGGTGGGGCT GCATTGCTTT
1401 ATGCGCTTTC GTCTCTAGAC GGTCTAAAAG GCAAGAATGA CGACGAACAA
1451 TGGGGTATAG ACATTATACG TCGCGCTGCT TGTGCTCCAA TCAAAAGAAT
1501 CATCAAGAAT TCTGGTTCTG AAGAAGCACC ATGCGTAATT CAACACTTGT
1551 TGAAGCAAAA CGACAAGGAA CTTATCTACA ATGTGGATAC TATGAACTAC
1601 GCGAATGCTT TTACATCTGG AGTTATGGAT CCTCTCAAAG TAGTACGTAT
1651 CGCGTTTGAT TTAGCTGTAT CACTCGCTGC AGTATTCATG ACTTTGAATG
1701 CAGTGGTTGT TGATGTTCCT AGTAAGAACG ACGCTGCTGG TGCTGGCGCT
1751 GGTGGTATGG GAGGCATGGG TGGTATG
```

FIG. 1B

```
      HGE agent   1 MSNTVVTGEVLDKSIREVVRILEDAVGCTAGPKGLTVAISKPYGSPEITK  50
                    |·|·||||| |||||||||||||||||||||||||||||||:|·||·||:||
     E. chaffeensis 1 MANVVVTGEQLDKSIREVVRILEDAVGCTAGPKGLTVAIGKSYGAPEVTK  50

51 DGYKVMKSIKPEEPLAAAIASIITQSASQCNDKVGDGTTTCSILTAKVIE 100
                    |||||:||||||:|||  |||·|||||||||||||||||||||||||||||
                 51 DGYKVIKSIKPEDPLALAIANIITQSASQCNDKVGDGTTTCSILTAKVIE 100

101 EVSKAKAAGSDIVSIKNGILKAKEAVLTALMSMRREV.EEDEIAQVATLS 149
                    ||||||||·|||:||:|:|||||||·|||||:|||  ·|:|||||||:|
                101 EVSKAKAAGADIVCIKEGVLKAKEAVLEALMSMKREVLSEEEIAQVATIS 150

150 ANGDKNIGSKIAQCVKEVGKDGVITVEESKGFKDLEVEKTDGMQFDRGYL 199
                    |||||||||||||·|||||||||||||||||||:|:|||||||||||||
                151 ANGDKNIGSKIAQCVQEVGKDGVITVEESKGFKELDVEKTDGMQFDRGYL 200

200 SPYFVTNAEKMLVEFENPYIFLTEKKINLVQSILPILENVARSGRPLLII 249
                    ||||||·|||||||||||||:||||:|::|·||||||||||||||||||
                201 SPYFVTNSEKMLVEFENPYILLTEKKLNIIQPILPILENVARSGRPLLII 250

250 AEDVEGEALSTLVLNKLRGGLQVAAVKAPGFGDRRKDMLGDIAVIVGAKY 299
                    |||||||||||||||||||||:|||||||||||||||||||||::·|||·
                251 AEDVEGEALSTLVLNKLRGGLHVAAVKAPGFGDRRKDMLGDIAILTGAKH 300

300 VVNDELAVKMEDIALSDLGTAKSVRITKDATTIIGSVDSSSESIASRTNQ 349
                    |:·|:||:||||·|·:||||·:|||||·|||||||||·||·:·||·|||
                301 VISDDLAIKMEDLTLAELGTAKNIRITKDTTTIIGSVDNSSANVQSRINQ 350

350 IKAQIENSSSDYDKEKLRERLAKLSGGVAVLKVGGSSEVEVKERKDRVED 399
                    || |||·|·||||||||||||||||||||||||||||||||||||||||
                351 IKMQIEASTSDYDKEKLRERLAKLSGGVAVLKVGGSSEVEVKERKDRVED 400

400 ALHATRAAVEEGVVPGGGAALLYALSSLDGLKGKNDDEQWGIDIIRRAAC 449
                    |||||||||||||||||||||||·|| |:·||:|||||:||·|·::||
                401 ALHATRAAVEEGVVPGGGAALLYTLSVLENLKSKNDDEQLGINIVKRALQ 450

450 APIKRIIKNSGSEEAPCVIQHLLKQNDKELIYNVDTMNYANAFTSGVMDP 499
                    ||||||||||||:|||||·||||||||||||:||||||:||||||||:||
                451 APIKRIIKNSGSENAPCVIAHLLKQNDKELIFNVDTMNFANAFTSGVIDP 500

500 LKVVRIAFDLAVSLAAVFMTLNAVVVDVPSKNDAAGAGAGGM........ 541
                    ||||||||:|||||||||||||:|||||||||·| |·||||||
                501 LKVVRIAFDFAVSLAAVFMTLNAIVVDVPSKDD.ANAGAGGMGGMGGMGG 549
```

FIG. 2

METHODS TO DETECT GRANULOCYTIC EHRLICHIOSIS

STATEMENT OF GOVERNMENT RIGHT

This invention was made with the support of grants from the National Institutes of Health (AI32403, AI39002 and AI37993). The U.S. Government has certain rights in the invention.

BACKGROUND OF THE INVENTION

Human granulocytic ehrlichiosis (HGE) is a recently described illness caused by a bacterial species that is phylogenetically similar to, or conspecific with, an ehrlichial genogroup comprising the veterinary pathogens *Ehrlichia equi* and *E. phagocytophilia* (Chen et al., *J. Clin. Micro.*, 32, 589 (1994); Dumler et al., *J. Clin. Micro.*, 33, 1098 (1995)). The only vectors demonstrated to transmit the HGE agent are Ixodes sp. ticks, although anecdotal evidence suggests that the American dog tick (*Dermacentor variabilis*) may also be implicated in HGE transmission. HGE typically presents as an acute febrile illness with headache, myalgias, leukopenia, thrombocytopenia, and elevated levels of alkaline phosphatase, lactate dehydrogenase, and aminotransferases (Bakken et al., *JAMA*, 272, 212 (1994); Bakken et al., *JAMA*, 275, 199 (1996); Pancholi et al., *J. Infect, Dis*, 172, 1007 (1995); Telford et al., *Proc. Natl. Acad. Sci USA*, 93, 6209 (1996)). Severe cases, when left untreated, may be fatal.

For the direct recovery of the HGE agent from clinical specimens, mouse inoculation, molecular detection, or cultivation of the organism in HL60 cells have been used. However, the duration of bacteremia with the HGE agent is not known, so the reliability of these tests beyond the acute stage of the illness has not been established. Antibody tests based on seroconversion to *E. equi* antigen have been used to identify infected persons after the initial stage of the illness (Bakken et al., *JAMA*, 272, 212 (1994); Bakken et al., *JAMA*, 275, 199 (1996)). However, the indirect fluorescent antibody (IFA) assay based on *E. equi* antigen is labor intensive, not widely available, and the interpretation of results is often subject to substantial individual variation (Bakken et al., *JAMA*, 275, 199 (1996); Dumler et al., supra; Dumler et al., *Dermat. Clinics*, 12, 25 (1994)).

Thus, what is needed is an improved method to detect the presence of an infectious agent associated with HGE.

SUMMARY OF THE INVENTION

The present invention is based upon the direct recovery (or isolation) of a gene encoding an immunogenic polypeptide associated with granulocytic ehrlichiosis in humans from patient tissues. Direct recovery of genes encoding immunodominant antigens from infected tissues, i.e., without prior growth in culture, is particularly useful to prepare immunodiagnostic reagents for emerging, uncultured, or difficult to culture, pathogens, e.g., the agents associated with human granulocytic ehrlichiosis (HGE), *Tropheryma whippelii*, the bacillary agent associated with Whipple's disease, and other organisms related to mycobacteria which are yet to be cultivated in vitro. Moreover, direct recovery of DNA comprising open reading frames can also facilitate development of customized immunodiagnostic reagents, even when recovery of the infectious agent is not possible or when extensive agent variability (i.e., "quasispecies") precludes development of universal immunodiagnostic reagents.

Thus, the invention provides an isolated and purified DNA molecule comprising a preselected DNA sequence encoding an immunogenic polypeptide, a biologically active subunit, or a biologically active variant thereof, the presence of which is associated with granulocytic ehrlichiosis in a mammal, e.g., in humans. Preferably, the preselected DNA sequence encodes an immunogenic polypeptide which is specifically associated with the agent which causes human granulocytic ehrlichiosis (HGE). A preferred embodiment of the invention provides a preselected DNA sequence which encodes an immunogenic polypeptide having an amino acid sequence comprising SEQ ID NO:2, e.g., the preselected DNA sequence comprises SEQ ID NO:1. The invention further provides an isolated and purified DNA molecule which is complementary to SEQ ID NO:1.

The invention also provides an expression cassette comprising a preselected DNA sequence operably linked to a promoter functional in a host cell wherein said DNA sequence encodes an immunogenic polypeptide, a biologically active variant or subunit thereof, wherein said polypeptide is associated with granulocytic ehrlichiosis in a mammal. The expression of the preselected DNA sequence in host cells yields a polypeptide which is an ehrlichial antigen. Preferably, the expression cassette of the invention comprises a preselected DNA sequence encoding an immunogenic fusion polypeptide, a portion of which comprises an ehrlichial-specific polypeptide. The remainder of the DNA sequence preferably encodes a polypeptide that enhances the immunogenicity of the fusion polypeptide in vivo.

As used herein, "an immunogenic polypeptide associated with granulocytic ehrlichiosis" is preferably a polypeptide having the amino acid Li sequence comprising SEQ ID NO:2, as well as variants of SEQ ID NO:2 which have at least about 80%, preferably at least about 90%, and more preferably at least about 95%, identity or homology to SEQ ID NO:2, or a biologically active subunit thereof. Biologically active subunits of the immunogenic polypeptide of the invention, and biologically active variants of the immunogenic polypeptide of the invention and subunits thereof, falling within the scope of the invention have at least about 10%, preferably at least about 50%, and more preferably at least about 90%, the activity of the polypeptide comprising SEQ ID NO:2. The activity of an immunogenic polypeptide of the invention can be measured by methods well known to the art including, but not limited to, the ability of the polypeptide to be bound by antibodies specific for the infectious agent associated with granulocytic ehrlichiosis (see Example II), or the ability of the polypeptide to elicit a sequence-specific immunologic response when the polypeptide is administered to an organism, e.g., a mammal such as rabbit, goat, sheep, rat or mouse. Preferably, the immunologic response is a humoral response, i.e, antibody response, directed to a particular epitope on the polypeptide. More preferably, the presence of antibodies specific for that epitope correlates with the granulocytic ehrlichiosis infection status of the organism.

Further provided is an isolated and purified immunogenic polypeptide, a biologically active subunit or variant thereof, which is associated with granulocytic ehrlichiosis in a mammal. The polypeptide is useful to detect the presence of antibodies in mammals, e.g., deer, mice, rats, dogs and humans, which are specific for an infectious agent associated with granulocytic ehrlichiosis. Preferably, the polypeptide has an amino acid sequence comprising SEQ ID NO:2. The isolated and purified polypeptides of the invention are useful to prepare an immunogenic composition, such as a vaccine comprising the polypeptide, in combination with a pharmaceutically acceptable carrier, wherein the administration of the immunogenic composition or vaccine to a mammal induces the production of antibodies to the polypeptide. In particular, an immunogenic composition or vaccine which comprises a polypeptide having an epitope which is specific for the agent associated with human granulocytic ehrlichiosis is preferred.

The invention provides a method of expressing a nucleic acid molecule encoding an immunogenic polypeptide, the presence of which is associated with granulocytic ehrlichiosis, in a cultured host cell stably transformed with a chimeric vector comprising said nucleic acid molecule operably linked to control sequences recognized by the host cell transformed with the vector, and recovering the polypeptide from the host cell.

The invention fturther provides a diagnostic method comprising contacting an amount of DNA obtained from a physiological sample which comprises cells from a mammal at risk of, or afflicted with, granulocytic ehrlichiosis, with an amount of at least two complementary oligonucleotides under conditions effective to amplify the DNA by a polymerase chain reaction so as to yield an amount of amplified DNA. At least one oligonucleotide binds specifically to a DNA sequence encoding a polypeptide derived or isolated from an infectious agent associated with granulocytic ehrlichiosis. The presence of the amplified DNA is then detected or determined. The presence of the amplified DNA is indicative of a mammal at risk of, or afflicted with, granulocytic ehrlichiosis. The results described below show that an amplified DNA was detected using DNA obtained from blood of two humans afflicted with granulocytic ehrlichiosis. Sequence and phylogenetic analysis of the polypeptide encoded by the amplified DNA shows that the polypeptide is homologous to the E. coli heat shock protein-60 (HSP60) and related to, but distinct from, a homologous protein found in E. chaffeensis (Sumner et al., Infection & Immunity, 61, 3546 (1993)) and from other rickettsia-like organisms known to infect humans.

Also provided is a method for detecting DNA encoding an immunogenic polypeptide associated with granulocytic ehrlichiosis in a mammal. The method comprises isolating or deriving an amount of DNA from a mammalian physiological sample which comprises cells suspected of containing DNA encoding the immunogenic polypeptide. The DNA is contacted with an amount of at least two oligonucleotides under conditions effective to amplify the DNA by a polymerase chain reaction so as to yield an amount of amplified DNA. At least one oligonucleotide is specific for the DNA encoding the immunogenic polypeptide. The presence of the amplified DNA is then determined or detected.

As used herein, the term an oligonucleotide "specific for the DNA encoding a polypeptide from an infectious agent associated with granulocytic ehrlichiosis" or "specific for DNA encoding an immunogenic polypeptide associated with granulocytic ehrlichiosis" means a DNA sequence that has at least about 80%, more preferably at least about 90%, and more preferably at least about 95%, sequence identity or homology to SEQ ID NO:1 An oligonucleotide or primer of the invention has at least about 7–50, preferably at least about 10–40, and more preferably at least about 15–35, nucleotides. Preferably, the oligonucleotide primers of the invention comprise at least 7 nucleotides at the 3' of the oligonucleotide primer which have at least about 80%, more preferably at least about 85%, and more preferably at least about 90%, identity to SEQ ID NO:1. Thus, the oligonucleotides of the invention may also include sequences which are unrelated to nucleic acid sequences of an infectious agent associated with granulocytic ehrlichiosis, e.g., they may encode restriction endonuclease recognition sequences. Preferred oligonucleotides of the invention include an oligonucleotide comprising SEQ ID NO:4, SEQ ID NO:5, SEQ ID NO:6, SEQ ID NO:8, SEQ ID NO:9 or SEQ ID NO:10.

Also provided is a diagnostic kit for detecting DNA which encodes at least a portion of a polypeptide specific to an infectious agent associated with granulocytic ehrlichiosis in a physiological sample suspected of containing said DNA. The kit comprises packaging containing, separately packaged, (a) a known amount of a first oligonucleotide, wherein the oligonucleotide consists of at least about 7–50 nucleotides, and wherein the oligonucleotide has at least about 80% identity to SEQ ID NO:1, and (b) a known amount of a second oligonucleotide, wherein the oligonucleotide consists of at least about 7–50 nucleotides, and wherein the oligonucleotide has at least about 80% identity to a nucleotide sequence which is complementary to SEQ ID NO:1.

Thus, the invention also provides an oligonucleotide which consists of at least about 7–50 nucleotides and which has at least about 80% identity to, or has complementarity to a nucleotide sequence having, SEQ ID NO:1.

Also provided is a method for detecting or determining the presence of antibodies in a mammalian physiological sample, which antibodies are specific for an infectious agent that is associated with granulocytic ehrlichiosis. The method comprises contacting an amount of purified polypeptide with the sample which is suspected of comprising antibodies specific for the infectious agent, for a sufficient time to form binary complexes between at least a portion of the antibodies and a portion of the purified polypeptide. The polypeptide is one which is expressed by, and is encoded by the nucleic acid of, the infectious agent. The presence or amount of the complexes is then determined or detected. The results reported hereinbelow demonstrated that a portion of purified polypeptide, expressed in vitro from a DNA molecule of the invention, is bound by antibodies from mice experimentally infected with the agent associated with human granulocytic ehrlichiosis. Thus, the detection of antibody responses to this and other ehrlichial antigens can be used in ELISA-based immunoassays for the serodiagnosis of granulocytic ehrlichial infection in animals and in humans.

Moreover, the results show that the expression of a gene encoding an antigenic polypeptide, wherein the gene is obtained by direct recovery from a clinical sample without the benefit of prior biological amplification via cultivation in vitro, is useful to detect a humoral immune response to an infectious agent, i.e., the agent associated with human granulocytic ehrlichiosis.

Further provided is a method for detecting granulocytic ehrlichiosis in a mammal. The method comprises contacting an amount of purified polypeptide with a sample suspected of containing antibodies to said polypeptide, for a sufficient time to form binary complexes between at least a portion of the antibodies and a portion of the purified polypeptide. The polypeptide is one which is encoded by the nucleic acid from an infectious agent associated with granulocytic ehrlichiosis. The presence or amount of the binary complexes is then determined or detected. The presence of said complexes is indicative of a mammal at risk of, or afflicted with, granulocytic ehrlichiosis.

Also provided is a diagnostic kit for detecting or determining antibodies that specifically react with an infectious agent which is associated with granulocytic ehrlichiosis. The kit comprises packaging, containing, separately packaged, a solid phase capable of binding a polypeptide and a known amount of a purified polypeptide, the presence of which is associated with granulocytic ehrlichiosis. Preferably, the polypeptide has an amino acid sequence comprising SEQ ID NO:2.

BRIEF DESCRIPTION OF THE FIGURES

FIG. 1. Nucleotide sequence (SEQ ID NO:1) encoding the heat shock protein-60 (HSP60 or groEL) homolog of the human granulocytic ehrlichiosis (HGE) agent.

FIG. 2. Alignment of the predicted amino acid sequence for-the HSP60 homologue encoded by a nucleic acid sequence associated with HGE (SEQ ID NO:2) and the HSP60 polypeptide encoded by *E. chaffeensis* DNA (SEQ ID NO:3).

FIG. 3. Neighbor-joining analysis of DNA sequences from several of the species having homology with the HGE agent-derived HSP60 homologue. Phylogenetic analysis was based on A) HSP60 gene sequences and B) 16S rRNA gene sequences. The bootstrap replicate percentages appear above each branch. The scale is provided as a measurement of the relative phylogenetic distance.

FIG. 4. Agarose gel and Southern blot analysis of PCR amplification products from Balb/C mouse blood and HL60 cells infected with the HGE agent. DNA isolated from Balb/C mouse blood and HL60 cells was subjected to PCR using primers Ehr521 and Ehr790. Lane 1, 100 bp molecular weight marker. Lanes 2–4, amplified DNA from the blood of Balb/C mice which were infected with a midwest strain (WI-1) of the HGE agent by syringe inoculation. Lane 5, amplified DNA from HL60 cells infected with a midwest strain (WI-1) of the HGE agent. Lane 6, blank. Lane 7, uninfected Balb/C mouse control. Lane 8, uninfected HL60 control. Lane 9, no DNA control. Lane 10, 100 bp molecular weight marker.

FIG. 5. Detection of murine serum antibody response to the HGE agent HSP60-like recombinant antigen.

A) Sera from Balb/C mice infected for 28 days by intraperitoneal inoculation with a midwest strain (WI-1) of the HGE agent or with *B. burgdorferi* strain N40. Lanes 1–2, uninfected mice. Lanes 3–5, mice infected by syringe inoculation with the HGE agent. Lanes 6–8, mice infected by syringe inoculation with $10^3$ *B. burgdorferi* strain N40. Lane 9, uninfected mouse. *E. equi* antibody titers are indicated above each lane.

B) Reactivity of mouse sera from Balb/C mice (see panel A) for glutathione-S transferase (GST). All lanes were incubated with anti-GST primary antibodies. Lane 1, recombinant GST-HGE HSP-60 fusion polypeptide. Lanes 2–3, sera from uninfected mice. Lanes 4–6, sera from mice infected with the HGE agent. Lanes 7–9, sera mice infected with *B. burgdorferi* strain N40. Lane 10, sera from an uninfected mouse. Lanes 11–12, blocking agent alone. Lane 13, 29 kD GST polypeptide.

C) Sera from C3H/HeJ mice infected by tick transmission with an east coast strain (NCH-1) of the HGE agent or with *B. burgdorferi* strain N40. Lanes 1–2, sera from mice infected with the HGE agent for six months. Lane 3, sera from a mouse that was fed upon by Ixodes sp. ticks infected with the NCH-1 strain of the HGE agent but was negative by blood smear and antibody response. Lanes 4–5, sera from mice infected for 19 months with the HGE agent. Lanes 6–9, sera from mice infected for six months with the HGE agent. Lane 10, sera from a mouse infected for less than one month with the HGE agent. Lane 11, sera from a mouse that was fed upon by Ixodes sp. ticks infected with the NCH-1 strain of the HGE agent but was negative by blood smear and antibody response. Lanes 12–14, sera from mice that were fed upon by uninfected Ixodes sp. ticks. Lanes 15–16, sera from mice infected for 10 months with *B. burgdorferi* strain N40. *E. equi* antibody titers are indicated above each lane.

DETAILED DESCRIPTION OF THE INVENTION

In order to better detect the infectious agent which causes, or is associated with, granulocytic ebrlichiosis, and in particular human granulocytic ehrlichiosis (HGE), granulocytic ehrlichiosis agent-specific DNA which encodes an immunogenic polypeptide is isolated from patients with the disease, or is isolated from non-human mammals or cell lines experimentally infected with the agent. Besides identifying the presence of infectious agent-specific nucleic acid sequences, or antibodies which bind to the polypeptide encoded by those nucleic acid sequences, in a mammal, the identification and isolation of these nucleic acid sequences or polypeptides may be useful to provide a clinically useful diagnostic test, or in molecular-based therapeutics.

Once a correlation has been established between the presence of the nucleic acid sequence, or antibodies to the polypeptide encoded by that sequence, and a particular disease, such as granulocytic ehrlichiosis or monocytic ehrlichiosis, mammalian physiological samples, e.g., tissue biopsies, blood sera or plasma, can be analyzed for the presence of the nucleic acid sequence, e.g., by an amplification reaction such as the polymerase chain reaction, or by screening sera for the presence of antibodies specific for the purified form of the polypeptide. The presence or amount of the nucleic acid molecule or antibodies in the mammalian sample can be compared to a control sample from a disease-free mammal.

An isolated and purified DNA molecule which encodes a polypeptide specific to the infectious agent can also be employed in an expression cassette to synthesize agent-specific polypeptides in vitro. In vitro prepared agent-specific polypeptide can be employed to prepare polyclonal or monoclonal antibodies specific for the agent, or in assays useful to detect the presence of agent-specific antisera in mammals. In vitro synthesized polypeptide may also be employed in a vaccine or immunogenic composition which, when administered to a mammal, can elicit antibodies which can inhibit or block subsequent infection of the host by the agent.

The DNA sequences (molecules) of the present invention are also useful to detect the replication or presence of the infectious agent in infected samples, to detect related DNA molecules and to amplify nucleic acid sequences, wherein said sequences can fall within the scope of the present invention.

Sources of Nucleic Acids Encoding an Immunogenic Polypeptide from the Granulocytic Ehrlichiosis Agent Sources of nucleotide sequences from which the present DNA molecules can be derived include nucleic acid from any mammalian cellular source, known or believed to be naturally or experimentally infected by a granulocytic ehrlichiosis, preferably a human granulocytic ehrlichiosis, causative agent, preferably derived from blood cells or cell lines derived therefrom, from which nucleic acid molecules can be isolated by methods well known to the art.

Isolation of a Gene Encoding a Granulocytic Ehrlichiosis-Specific Immunogenic Polypeptide A nucleic acid molecule encoding an immunogenic, granulocytic ehrlichiosis agent-specific polypeptide, can be identified and isolated using standard methods, as described by Sambrook et al., *Molecular Cloning: A Laboratory Manual*, Cold Spring Harbor, N.Y. (1989). For example, polymerase chain reaction (PCR) can be employed to isolate and clone HGE agent-specific genes. "PCR" refers to a procedure or technique in which amounts of a preselected fragment of nucleic acid, RNA and/or DNA, are amplified as described in U.S. Pat. No. 4,683,195.

In PCR, sequence information from the ends of the region of interest or beyond is employed to identify and synthesize oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erhlich, ed., *PCR Technology*, (Stockton Press, NY, 1989).

Thus, primers are made to correspond to DNA encoding highly conserved regions of polypeptides or to nucleotide sequences which were identified and compared to generate the primers, e.g., by a sequence comparison of other bacterial HSP60 genes. At least two primers are prepared, one of which is predicted to anneal to the antisense strand, and preferably one of which is predicted to anneal to the sense strand of a DNA molecule which encodes the immunogenic polypeptide. The products of each PCR reaction are separated via an agarose gel and all consistently amplified products can be gel-purified and cloned directly into a suitable vector, such as a plasmid vector. The resultant plasmids are subjected to restriction endonuclease and dideoxy sequencing of double-stranded plasmid DNAs.

Another approach to identify, isolate and clone genes which encode a polypeptide associated with the granulocytic ehrlichiosis causative agent is to screen a cDNA library generated from infected tissues, e.g., formed from DNA from HGE agent-infected blood cells. Screening for DNA fragments that encode all or a portion of a gene encoding an immunogenic, granulocytic ehrlichiosis agent-specific polypeptide can be accomplished by probing the library with a probe, which comprises sequences that are highly conserved between genes believed to be related to the gene encoding the immunogenic polypeptide, e.g., HSP60 gene probe, or by screening of plaques for binding to antibodies from a mammal that has been infected by the granulocytic ehrlichiosis agent. DNA fragments that bind to the probe, or which are immunoreactive with antibodies, can be subcloned into a suitable vector and sequenced and/or used as probes to identify other cDNA or genomic sequences encoding all or a portion of the immunogenic polypeptide.

As used herein with respect to a DNA molecule or polypeptide, the terms "isolated and/or purified" refer to in vitro isolation of a DNA or polypeptide molecule from its natural cellular environment, and from association with other components of the cell, such as nucleic acid or protein, so that it can be sequenced, replicated, and/or expressed. For example, "isolated granulocytic ehrlichiosis agent-specific nucleic acid" is RNA or DNA containing greater than 7, preferably 15, and more preferably 20 or more, sequential nucleotide bases. The sequential nucleotide bases encode a biologically active granulocytic ehrlichiosis, preferably an HGE, agent-specific polypeptide or a fragment thereof, or a biologically active variant granulocytic ehrlichiosis, preferably an HGE, agent-specific polypeptide or a fragment thereof. The DNA or RNA is complementary to the non-coding strand, or complementary to the coding strand, of RNA or DNA from the agent which causes, or is associated with, granulocytic ehrlichiosis and not complementary to the RNA or DNA from related organisms which do not cause, or are not associated with, granulocytic ehrlichiosis, or hybridizes to said RNA or DNA and remains stably bound under stringent conditions.

Thus, the RNA or DNA is "isolated" in that it is free from at least one contaminating nucleic acid with which it is normally associated in the natural source of the RNA or DNA, and the isolated RNA or DNA is preferably substantially free of any other mammalian RNA or DNA. The phrase "free from at least one contaminating source of nucleic acid with which it is normally associated" includes the case where the nucleic acid is reintroduced into the source or natural cell but is in a different chromosomal location or is otherwise flanked by nucleic acid sequences not normally found in the source cell. An example of isolated HGE agent-specific nucleic acid is RNA or DNA that encodes a biologically active, i.e., immunogenic, HGE agent-specific polypeptide sharing at least about 80%, preferably at least about 90%, sequence identity with the HGE agent-specific polypeptide of FIG. 2.

As used herein, the term "recombinant nucleic acid" or "preselected nucleic acid," e.g., "recombinant DNA sequence or segment" or "preselected DNA sequence or segment" refers to a nucleic acid, i.e., to DNA that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

Variants of the DNA Molecules of the Invention

Nucleic acid molecules encoding amino acid sequence variants of an granulocytic ehrlichiosis agent-specific immunogenic polypeptide, e.g., HSP60, can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of a granulocytic ehrlichiosis agent-specific polypeptide.

Oligonucleotide-mediated mutagenesis is a preferred method for preparing amino acid substitution variants of the granulocytic ehrlichiosis agent-specific polypeptide. This technique is well known in the art as described by Adelman et al., *DNA*, 2, 183 (1983). Briefly, granulocytic ehrlichiosis agent-specific DNA is altered by hybridizing an oligonucleotide encoding the desired mutation to a DNA template, where the template is the single-stranded form of a plasmid or bacteriophage containing the unaltered or native DNA sequence encoding a granulocytic ehrlichiosis agent-specific polypeptide. After hybridization, a DNA polymerase is used to synthesize an entire second complementary strand of the template that will thus incorporate the oligonucleotide primer, and will code for the selected alteration in the DNA encoding the granulocytic ehrlichiosis agent-specific polypeptide.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci, U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed so that one strand of DNA encodes the mutated form of the granulocytic ehrlichiosis agent-specific polypeptide, and the other strand (the original template) encodes the native, unaltered sequence of the granulocytic ehrlichiosis agent-specific polypeptide. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified so that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

A preferred embodiment of the invention is an isolated and purified DNA molecule comprising a preselected DNA sequence encoding a granulocytic ehrlichiosis agent-specific HSP60 polypeptide comprising SEQ ID NO:2, wherein the DNA segment comprises SEQ ID NO:1. Variants of SEQ ID NO:2 having nucleotide substitutions which are "silent" are also within the scope of the invention. That is, when nucleotide substitutions are present in a codon, the same amino acid is encoded by the codon with the nucleotide substitution as is encoded by the codon without the substitution. For example, leucine is encoded by the codons TTA, TTG, CTT, CTC, CTA and CTG. A variant of SEQ ID NO:1 at the eleventh codon in the mature polypeptide (TTA in SEQ ID NO:1) includes the substitution of TTG for TTA. Other "silent" nucleotide substitutions in SEQ ID NO:1 which can encode a polypeptide having SEQ ID NO:2 can be ascertained by reference to page D1 in Appendix D in Sambrook et al., *Molecular Cloning: A Laboratory Manual* (1989). Nucleotide substitutions can be introduced into DNA segments by methods well known to the art. See, for example, Sambrook et al., supra.

Chimeric Expression Cassettes

To prepare recombinant polypeptides useful to detect antibodies which bind to the granulocytic ehrlichiosis agent, an expression cassette is prepared comprising a preselected DNA sequence which encodes a granulocytic ehrlichiosis agent-specific immunogenic polypeptide operably linked to a promoter. Preferably, the immunogenic polypeptide is a fusion polypeptide.

Generally, the expression cassette is in the form of chimeric DNA, and comprises plasmid DNA that can also contain coding regions flanked by control sequences which promote the expression of the preselected DNA segment once the expression cassette is introduced into a host cell. As used herein, "chimeric" means that a vector comprises DNA from at least two different species, or comprises DNA from the same species, which is linked or associated in a manner which does not occur in the "native" or wild type of the species. Aside from preselected DNA sequences that serve as transcription units for granulocytic ehrlichiosis agent-specific polypeptides or portions thereof, a portion of the preselected DNA may be untranscribed, serving a regulatory or a structural finction. For example, the preselected DNA may itself comprise a promoter that is active in bacterial, fungal, insect or mammalian cells, or may utilize a promoter already present in the genome that is the transformation target. There are many promoter elements well known to the art that may be employed in the practice of the invention.

Other elements functional in the host cells, such as introns, enhancers, polyadenylation sequences and the like, may also be a part of the preselected DNA. Such elements may or may not be necessary for the finction of the DNA, but may provide improved expression of the DNA by affecting transcription, stability of the MRNA, or the like. Such elements may be included in the DNA as desired to obtain the optimal performance of the transforming DNA in the cell.

"Control sequences" are defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a prepolypeptide that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable polypeptides are well known in the art. In general, a reporter gene is a gene which is not present in or expressed by the recipient Aorganism or tissue and which encodes a polypeptide whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

Transformation into Host Cells

The recombinant DNA can be readily introduced into host cells, e.g., mammalian, bacterial, fungal or insect cells by transfection with an expression vector comprising DNA encoding a granulocytic ehrlichiosis agent-specific polypeptide by any procedure useful for the introduction into a particular cell, e.g., calcium phosphate precipitation, lipofection, electroporation, and the like, to yield a transformed cell having the cDNA stably integrated into its genome, so that the DNA molecules, sequences, or segments, of the present invention are expressed by the host cell. That is, the present invention also provides a transformed host cell having a genome augmented by a recombinant (non-native) DNA sequence, preferably by a chromosomally integrated recombinant (genetically engineered) DNA sequence that includes a gene encoding a granulocytic ehrlichiosis agent-specific polypeptide.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of prokaryotic origin, but cell lines or host cells of eukaryotic origin may be employed, including plant, insect, yeast, fungal or mammalian sources. Generally, the preselected DNA sequence is not resident in the genome of the uninfected host cell.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA is isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence.

Granulocytic Ehrlichiosis Agent-Specific Polypeptides

The present invention provides an isolated, purified granulocytic ehrlichiosis agent-specific polypeptide, which can be prepared by recombinant DNA methodologies. The general methods for isolating and purifying a recombinantly expressed polypeptide from a host cell are well known to those in the art. Examples of the isolation and purification of such polypeptides are given in Sambrook et al., cited supra. Moreover, since the present invention provides the amino acid sequence of an HGE agent-specific polypeptide (FIG. 2), it or bioactive variants thereof can also be synthesized by the solid phase peptide synthetic method. This established and widely used method, including the experimental procedures, is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285.

When a granulocytic ehrlichiosis agent-specific polypeptide is expressed in a recombinant cell it is necessary to purify the polypeptide from other recombinant cell proteins or polypeptides to obtain preparations that are substantially homogenous as to the granulocytic ehrlichiosis agent-specific polypeptide. For example, the culture medium or lysate can be centrifuged to remove particulate cell debris. The membrane and soluble protein fractions are then separated. The granulocytic ehrlichiosis agent-specific polypeptide may then be purified from the soluble protein fraction. Alternatively, the granulocytic ehrlichiosis agent-specific polypeptide may be purified from the insoluble fraction, i.e., refractile bodies (see, for example, U.S. Pat. No. 4,518,526). Granulocytic ehrlichiosis agent-specific polypeptide may be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography, and the like.

If expressed as a fuision polypeptide, the fusion polypeptide may be purified by methods specific for the non-granulocytic ehrlichiosis agent-specific portion of the polypeptide. For example, if the fusion polypeptide is a glutathione-S transferase (GST) fusion polypeptide, GST 4B beads may be employed to purify the fusion polypeptide.

Granulocytic ehrlichiosis agent-specific polypeptide, variant granulocytic ehrlichiosis agent-specific polypeptide, or a biologically active subunit thereof can also be prepared by in vitro transcription and translation reactions. A granulocytic ehrlichiosis agent-specific expression cassette can be employed to generate granulocytic ehrlichiosis agent-specific transcripts which are subsequently translated in vitro so as to result in a preparation of substantially homogenous granulocytic ehrlichiosis agent-specific polypeptide, variant granulocytic ehrlichiosis agent-specific polypeptide, or a biologically active subunit thereof. The construction of vectors for use in vitro transcription/translation reactions, as well as the methodologies for such reactions, are well known to the art.

Once isolated from the resulting transgenic host cells or from in vitro transcription/translation reactions, derivatives and chemically derived variants of the granulocytic ehrlichiosis agent-specific polypeptide can be readily prepared. For example, amides of the granulocytic ehrlichiosis agent-specific polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the granulocytic ehrlichiosis agent-specific polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal granulocytic ehrlichiosis agent-specific amino acid sequence, for example the HGE agent-specific amino acid sequence of FIG. 2, can be modified by substituting one or two conservative amino acid substitutions for the positions specified, including substitutions which utilize the D rather than L form.

The invention also provides variant or modified forms of the granulocytic ehrlichiosis agent-specific polypeptide, e.g., the HGE agent-specific HSP60 polypeptide. One or more of the residues of this polypeptide can be altered, so long as the variant polypeptide has at least about 10%, preferably at least about 50%, and more preferably at least about 90%, of the biological activity of the granulocytic ehrlichiosis polypeptide, e.g., the polypeptide having SEQ ID NO:2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

Granulocytic Ehrlichiosis Agent-Specific Variant Polypeptides

Variant granulocytic ehrlichiosis agent-specific polypeptides will have at least one amino acid substitution relative to the polypeptide sequence of a particular granulocytic ehrlichiosis-agent isolate, e.g., SEQ ID NO:2. In particular, amino acids are substituted in a relatively conservative manner. Such conservative substitutions are shown in Table 1 under the heading of exemplary substitutions. More preferred substitutions are under the heading of preferred substitutions. After the substitutions are introduced, the products are screened for biological activity.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the antigenic site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp,glu;

(4) basic: asn, gln, his, lys, arg;

(5) residues that influence chain orientation: gly, pro; and (6) aromatic; trp, tyr, phe.

The invention also envisions granulocytic ehrlichiosis agent-specific polypeptide variants with non-conservative substitutions. Non-conservative substitutions entail exchanging a member of one of the classes described above for another. Amino acid substitutions are introduced into the DNA molecules of the invention by methods well known to the art. For example, see the description hereinabove for the introduction of silent mutations into the DNA molecules of the invention.

Detection of Granulocytic Ehrlichiosis Agent-Specific DNA by Polymerase Chain Reaction (PCR)

To detect a DNA encoding a granulocytic ehrlichiosis agent-specific polypeptide, DNA is isolated from a cellular sample suspected of containing granulocytic ehrlichiosis agent associated DNA, e.g., DNA isolated from a human suspected of having HGE. The DNA can be isolated by methods known to the art. See Sambrook et al., supra. The isolated DNA is mixed with primers specific for the granulocytic ehrlichiosis agent DNA so as to yield amplified, HGE agent-specific DNA product. Preferably, a hemi-nested PCR is employed. For example, primers such as BR588 (5'YGG ATA YCT TTC KCC TTA YTT T 3'; SEQ ID NO:8), SP949 (5'CTT GGT ACT GCT AAG AGC GTG 3'; SEQ ID NO:9) or BR1212 (5'CCT TCC TCA ACA GCA GCT CTA 3'; SEQ ID NO:10) may be useful to detect HGE agent-specific sequences when employed in a hemi-nested PCR.

To detect the PCR amplified product, the reaction mixture is typically subjected to agarose gel electrophoresis or another separation technique, and the presence or absence of the granulocytic ehrlichiosis agent-specific amplified DNA is detected. Detection of the amplified granulocytic ehrlichiosis agent DNA may be accomplished by excising or eluting the fragment from the gel (for example, see Lawn et al., Nucleic Acids Res., 9, 6103 (1981), and Goeddel et al., Nucleic Acids Res., 8, 4057 (1980)), cloning the amplified product into a cloning site of a suitable vector and sequencing the cloned insert. Alternatively, the granulocytic ehrlichiosis agent-amplified DNA may be detected using Southern hybridization with a granulocytic ehrlichiosis agent-specific oligonucleotide probe, or comparing its electrophoretic mobility with DNA standards of known molecular weight.

Uses of Recombinant Granulocytic Ehrlichiosis Agent-Specific Polypeptides

Once isolated, granulocytic ehrlichiosis agent-specific polypeptide and its antigenically active variants, derivatives and fragments thereof can be used in assays for the detection of the presence of the granulocytic ehrlichiosis agent in samples derived from biological materials suspected of containing the polypeptide or anti-polypeptide antibodies. Thus, the polypeptide can be used as a "capture antigen" to bind to anti-polypeptide antibodies in a sample of a mammalian physiological fluid. For example, a physiological sample comprising antibodies is mixed with purified granulocytic ehrlichiosis agent-specific polypeptide so as to yield a binary complex. The antibodies which are bound to the polypeptide are separated from the antibodies which are not bound to the polypeptide. Then the complex is detected or determined. Preferably, the complex is detected by an anti-mammal IgG antibody (sheep, goat, mouse, rat human etc.).

The invention will be further described with reference to the following Examples.

EXAMPLE I

Isolation and Sequence of the HSP60 (groEL) Homologue from the HGE Agent

To provide an improved method to detect the infection of a mammal by the HGE agent, the DNA sequences which encode a conserved polypeptide, i.e., the HSP60 protein, of organisms which are closely related to the HGE agent, e.g., E. chaffeensis and Cowdria ruminantium (GenBank accession numbers L10917 and U13638, respectively), were aligned using the GAP algorithm of the Wisconsin package. From this alignment, several broad-range PCR primer sets were synthesized (Integrated DNA Technologies, Coralville, Iowa) from regions conserved among the two genes (Table 2).

One hundred (100) pmol of primer HSP961 (SEQ ID NO:4) and HSP1754a (SEQ ID NO:5) (Table 2) were incorporated into a PCR master mix containing 10% glycerol, 1X PCR buffer II (Perkin Elmer Corp., Norwalk, Conn.), 2.0 mM $MgCl_2$ (Perkin Elmer Corp.), 200 µM each of DATP, dGTP, and dCTP, 100 µM each of dTTP and dUTP, 2.5 units of Amplitaq DNA polymerase (Perkin Elmer Corp.) and 5 µl of a patient DNA sample. Patient DNA was obtained by extracting DNA from whole blood samples from two human patients with the IsoQuick Nucleic Acid Extraction Kit (Orca Research Inc., Bothell, Wash.) as previously described (Kolbert, in: PCR Protocols for Emerging Infectious Diseases, ASM Press, Washington, D.C. (1996)). The isolated DNA was stored at 4° C. prior to amplification. The two patients,were previously confirmed to have HGE by clinical presentation, antibody titer to E. equi, and by PCR analysis for a portion of the 16S rDNA gene.

Amplification was performed in a 100 µl reaction volume with a Temptronic thermal cycler (Barnstead-Thermolyne, Dubuque, Iowa) using the following parameters: 94° C. incubation for 4 minutes, then 40 cycles at 94° C. for 45 seconds, 60° C. for 45 seconds, 72° C. for 45 seconds, followed by a 72° C. incubation for 5 minutes. Subsequent to PCR amplification, a 10 µl aliquot of each amplification product was electrophoresed in a 2% agarose gel (Seakem GTG, FMC Bioproducts, Rockland, Me.) to assess amplification integrity and the remainder was purified (Qiaquick PCR purification kit, Qiagen Inc., Chatsworth, Calif.) in preparation for DNA sequencing.

PCR amplification of each of the two patient DNA samples produced an 820 bp product. The amplicon was sequenced on an ABI 373 or ABI 377 automated DNA sequencing instrument (Perkin Elmer Applied Biosystems Division, Foster City, Calif.) and the consensus sequence was then used as a query in the GenBank sequence database in order to identify homologous sequences (FASTA algorithm of the Wisconsin package, Genetics Computer Group, Program Manual, 8th ed.). The sequences which were most closely related to the query sequence were the HSP60 homologs from E. chaffeensis and C. ruminantium with 76.5% and 76.3% nucleotide sequence identity, respectively.

TABLE 2

Nucleotide sequence and function of oligonucleotide primers used
for recovery and sequencing HSP60 homologue of the HGE agent

| Primer designation | Nucleotide sequence | SEQ ID NO: | Function |
|---|---|---|---|
| Ehr20[a] | GCAAGCTTAAGACATGCAAGTC | 11 | 16S rDNA PCR/sequencing |
| Ehr241[a] | CCAGGTATAGATCATCGCC | 12 | 16S rDNA PCR/sequencing |
| HSP961[b] | GAAGAAATTGCHCAAGTWGC | 4 | HSP PCR/sequencing |
| HSP1754a | TTCTTCAACAGCWGCTCTAG | 5 | HSP PCR/sequencing |
| HSP354 | CGYCAGTGGGCTGGTAATGAA | 6 | HSP PCR/sequencing |
| HSP2165 | CCATACCWCCCATGCCTC | 7 | HSP PCR/sequencing |
| HSP437 | CAAACAACCGTAGCATAAGACTAT | 13 | HSP sequencing |
| HSP577 | AAATCAATTAGAGAAGTTGT | 14 | HSP sequencing |
| HSP611 | TAGGACCAGCAGTACAACCAACTGCAT | 15 | HSP sequencing |
| HSP759 | TACTCAGAGTGCTTCTCAGTGTAATGA | 16 | HSP sequencing |
| H5P857 | CAATATCAGATCCAGCAGCTT | 17 | HSP sequencing |
| HSP1049 | AAGACGGTGTTATAACTGTTGAAG | 18 | HSP sequencing |
| HSP1066 | AAKCCTTTRCTTTCTTCAAC | 19 | HSP sequencing |
| HSP1411 | GATATTGCTGTAATAGTAGGCGCTA | 22 | HSP sequencing |
| HSP1505 | CTTTTGTGATTCGCACGCTCT | 23 | HSP sequencing |
| HSP1668 | TGGCGTTGCTGTACTCAAGGT | 24 | HSP sequencing |
| HSP1719 | CATCTTCTACTCTGTCTTTGCGT | 25 | HSP sequencing |
| HSP1750 | TCAACAGCAGCTCTAGTTGC | 26 | HSP sequencing |
| HSP1754s | CTAGAGCTGCTGTTGAAGAA | 27 | HSP sequencing |
| HSP1766 | ACCAGGTACTACACCTTCCTCAA | 28 | HSP sequencing |

In order to recover the complete open reading frame of the HSP60 homologue from the HGE agent, consensus PCR was performed on HL60 cell cultures co-cultivated with mouse PMNs (see below) isolated from a SCID (C.B-17) mouse that was previously infected with patient blood. The patient had clinical and laboratory confirmed HGE infection. Transmission of the HGE agent from the patient to mice was accomplished by intraperitoneal inoculation of 100 μl of blood from the patient into four week-old C.B-17 scid/scid mice (n=3). Twenty eight days following inoculation, 100 μl of blood was obtained from each mouse by puncture of the peri-orbital sinus and DNA was extracted using the IsoQuick Nucleic Acid Extraction Kit (Orca Research Inc.).

Ehrlichial 16S rDNA was detected in mouse blood by PCR using 16S ehrlichial group-specific primers (e.g., Ehr20(SEQ ID NO:11), and Ehr241(SEQ ID NO:12); Table 2). PCR amplification reaction mixes and cycling conditions were identical to those described above for the broad-range HSP60 amplifications with the exception that the cycle number was increased to 50 cycles. Subsequent to PCR, 10 μl of PCR product was electrophoresed in a 2% agarose gel (Seakem GTG, FMC Bioproducts) to assess amplification integrity and the DNA was transferred by Southern blot to a nylon membrane. The presence of ehrlichial 16S rDNA was confirmed by hybridization with an internal probe amplified by PCR primers Ehr552 and Ehr706 (Pancholi et al., J. Infect, Dis., 172, 1007 (1995)). Sequence analysis of the PCR product confirmed that the isolate was HGE (subsequently referred to as the WI-1 HGE isolate).

After confirmation of the transmission of the HGE causative agent, whole blood was obtained from the infected mice by cardiac puncture and the polymorphonuclear leukocytes (PMNs) were isolated by gradient centrifugation. The PMNs were resuspended in Hank's balanced salt solution (Bio Whittaker, Inc., Walkersville, Md.), and quantitated microscopically in a cell counting chamber. Mouse PMNs were co-cultivated with HL-60 human promyelocytic leukemia cells (ATCC CCL 240, American Type Culture Collection, Rockville, Md.) at a ratio of 1:2 in RPMI 1640 media (Bio Whittaker, Inc.) containing 15% fetal calf serum and the infection status of cultured cells was monitored by PCR, as described above for infected mice. DNA was extracted using the IsoQuick kit (Orca Research) from approximately $1.5 \times 10^6$ co-cultivated PMN and HL-60 cells 9 days following exposure of the HL-60 cells to infected mouse PMNs.

Broad-range PCR primers HSP354 (SEQ ID NO:6) and HSP2165 (SEQ ID NO:7) (Table 2) were used to perform duplicate amplifications of DNA isolated from HGE agent-infected HL60 cells. Five μl of the isolated DNA was added to a master mix prepared according to manufacturer's instructions for the Expand High Fidelity PCR System (Boehringer Mannheim Corporation, Indianapolis, Ind.), with the exceptions that a) 50 pmol of each primer was used in a 100 μl reaction and b) samples were thermal cycled at 94° C. for 4 minutes, then 35 cycles at 94° C. for 1 minute, 58° C. for 1 minute, and 72° C. for 2 minutes, and incubated at 72° C. for 10 minutes. The amplified products were electrophoresed in a 1% Seaplaque agarose gel (FMC Bioproducts), the appropriate band was excised, and the DNA products were pooled and purified according to the manufacturer's instructions for the Wizard PCR prep (Promega Corp., Madison, Wis.).

An approximately 1.8 kb fragment was amplified from the HGE agent-infected cell cultures. Both strands of the product were sequenced with internal primers designed to create overlapping sequences, and a sequence database search was performed on each sequence. The overlapping sequences were then aligned with the Assemblylign Sequence Assembly software package (Oxford Molecular, Campbell, Calif.) and the contiguous 1.6 kb sequence (SEQ ID NO:1; FIG. 1) was used as a query sequence in GenBank to search for related sequences.

Of the related sequences, C. ruminantium, E. chaffeensis, Chlamydia pneumoniae, Rickettsia tsutsugamushi, Bartonella bacilliformis, and E. risticii, were aligned with the ehrlichial sequence using the Pileup algorithm of the Wisconsin package. The Escherichia coli HSP60 gene was included as an outgroup. As previously determined from the human blood-derived sequence, the sequence generated from the HGE agent-infected HL60 cells was most closely related to cognate genes from E. chaffeensis and C. ruminantium with sequence identity of 75.6% and 75.2%, respectively.

The approximate 1.8 kb DNA segment was then aligned with the *E. chaffeensis* HSP60 sequence by using the GAP algorithm of the Wisconsin package. The alignment indicated that the HGE agent DNA sequence encoding HSP60 comprises a nearly complete open reading frame (ORF), including the ribosomal binding site and start codon, but lacks the terminal 33 bp. The sequence contains 43.3% GC content as compared to *E. chaffeensis* which contains 34.5% GC. Alignment of the predicted HSP60-like amino acid sequences from *E. chaffeensis* and the HGE agent indicated 93.6% amino acid similarity (FIG. 2). The codon usage for the HGE agent HSP60-like sequence was similar to that seen in the homologous *E. chaffeensis* sequence for most amino acids, but codon preferences reflected the higher GC content seen in the HGE agent. In addition, the HGE-specific ORF contained an unusual TGG codon for tryptophan which is not seen in *E. chaffeensis* or in the *E. coli* HSP60 gene sequence.

Phylogenetic analysis of the alignment generated by the Wisconsin package was accomplished with the Molecular Evolutionary Genetics Analysis MEGA) 1.01 computer program (Kumar et al., 1.01 ed (1993)). A Jukes-Cantor istance measurement was established and neighbor-joining analysis was performed ith 500 bootstrap replicates. Further data analysis was achieved with the hylogenetic Analysis Using Parsimony (PAUP) 3.1.1 computer program (Swofford, 3.1.1 ed. (1993)). A branch and bound algorithm with 100 bootstrap replicates was used to confirm the branching order observed with the neighbor-joining analysis.

Phylogenetic analyses showed the HGE agent ORF was closely related to those of *C. ruminantium* and *E. chaffeensis* (FIG. 3A). However, both neighbor-joining and parsimony analysis indicated that *C. ruminantium* and *E. chaffeensis* clustered together in 100% of the bootstrap replicates, to the exclusion of the HGE agent. Rickettsial species *E. risticii* and *Rickettsia tsutsugamushi* clustered with *C. ruminantium, E. chaffeensis*, and the HGE agent in 98% and 99% of the bootstrap replicates, respectively, yet did not occupy the same terminal branches.

Figure 3B:
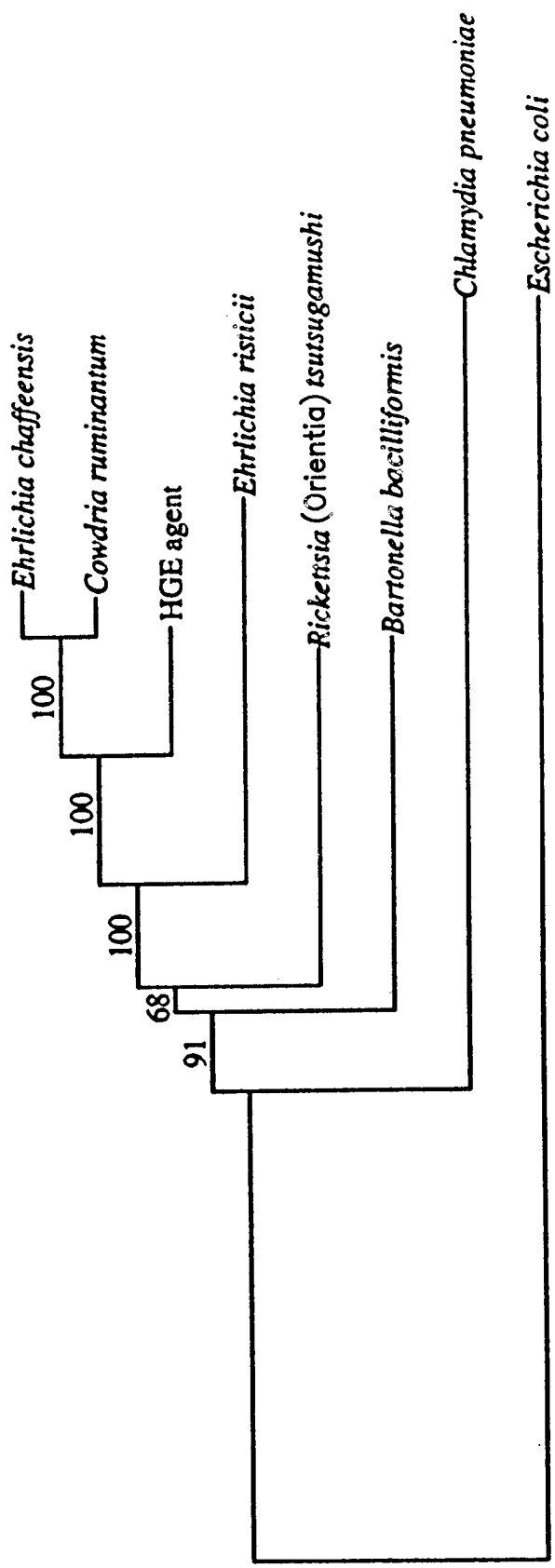

A similar branching order was provided by analysis of the 16S rRNA gene (FIG. 3B). Although it is an arthropod-borne pathogen, with epicellular growth characteristics, *Bartonella bacilliformis* clustered with *E. coli* and segregated from the rickettsia-like agents in 91% of the bootstrap replicates.

Thus, sequence analysis of the HSP60 gene of the HGE agent suggests that the ehrlichial agents associated with HGE are closely related, and that three sequences recovered from patients are similar to, but not identical to, HSP60-like genes described for other bacterial organisms.

EXAMPLE 2

Preparation of an HGE Agent Specific Fusion Polypeptide

Useful to Detect Anti-Ehrlichial Antibodies

An 820 bp DNA segment was generated by PCR amplification of HGE-agent infected patient DNA samples with the broad-range primer set HSP961 (SEQ ID NO:4)/HSP1754 (SEQ ID NO:5). The PCR product was electrophoresed in a 2% agarose gel (Seaplaque GTG, FMC Bioproducts), the resulting band was excised, and the DNA was purified by hot phenol extraction and ethanol precipitation (Sambrook et al., *Molecular Cloning*: A Laboratory Manual, Cold Spring Harbor Press (1989)). Single-stranded overhangs were created by digestion with restriction enzymes XbaI and HindII, resulting in a 540 bp unidirectional insert.

A pGEX-KG plasmid vector (Pharmacia Biotech, Piscataway, N.J.) was purified by CsCl gradient (Sambrook et al., supra) and digested with XbaI and HindIII. The 540 bp insert was then ligated into the pGEX-KG vector to yield a plasmid that encodes a glutathione S-transferase fusion polypeptide (Glutathione S-Transferase (GST) Gene Fusion System (Pharmacia Biotech Inc.)). Competent *E. coli* DH5 cells (Gibco-BRL, Gaithersburg, Md.) were used for the initial transformation and maintenance of the insert containing plasmid. Appropriate colonies were chosen and the plasmid was then transformed into *E. coli* BL21 cells for expression of a GST fuision polypeptide. The GST fusion polypeptides were purified by affinity chromatography on glutathione S-transferase 4B beads (Pharmacia Biotech.).

In order to visualize the recombinant GST fusion polypeptide, a 3 μg sample was electrophoresed in a 12% separating/5% stacking SDS-PAGE analytical gel overnight at 80 v and then stained with Coomassie blue. A 45 kDa fission polypeptide was observed by SDS-PAGE analysis.

In order to purify the recombinant GST fusion polypeptide, a preparative 12% separating/5% stacking SDS-PAGE gel was loaded with 30 μg of the GST fusion polypeptide and electrophoresed overnight at 80 v. The GST fuision polypeptide was transferred by Western blot onto a polyvinylidendifluoride (PVDF) membrane (Immobilon-P, Millipore, Bedford, Mass.) for 5 hours at 350 mA in a Hoefer Transphor Tank Electrotransfer Unit (Model TE42, Hoefer Scientific, San Francisco, Calif.) using TOWBIN buffer (192 mM glycine, 25 mM TRIS, pH 8.3, 15% methanol).

Western blots of the recombinant GST fusion polypeptide were employed to detect serum antibody to the HGE agent. Serum antibody directed against the HGE agent in experimentally infected Balb/C mice (infected by syringe inoculation), infected CEH/HeJ mice (infected by tick transmission), and noninfected control mice was qualitatively detected with the Chemiluminescent Blotting Substrate (POD) kit (Boehringer Mannheim Corp., Indianapolis, Ind.) according to manufacturer's instructions. Briefly, mouse serum was diluted 1:250 in 0.5% blocking solution, then applied to the membrane enclosed in a 25 well miniblotter cassette (Immunetics, Inc., Cambridge, Mass.) and incubated at room temperature for 1 hour on a rocking platform. The blot was washed twice in TRIS buffered sodium chloride with tween 20 (TBST) for 10 minutes and twice in a 0.5% blocking solution for 10 minutes.

A secondary reagent of goat anti-mouse Ig polyvalent peroxidase conjugate (Boehringer Mannheim Corp.) diluted 1:4000 in 0.5% blocking solution was added and the membrane was rocked for 30 minutes at room temperature. Blots were exposed to detection reagents and autoradiography was performed with Kodak X-Omat AR fihn (Eastman Kodak, Rochester, N.Y.). Results obtained by Western blot for the detection of antibodies specific for the HSP60-homologue of the HGE agent were confinned by an indirect fluorescent antibody assay for *E. equi* antigen (Linmed, Biologics, Brea, Calif.). Sera were screened at a starting dilution of 1:64 in PBS. Fluorescein-conjugated goat anti-mouse IgG was used to detect specific fluorescence of *E. equi*.

Figure 4A:
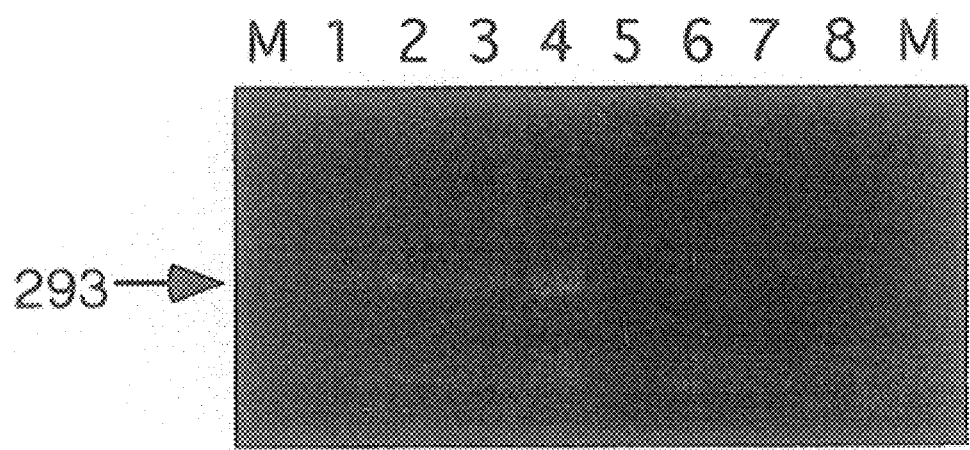
Figure 4B:
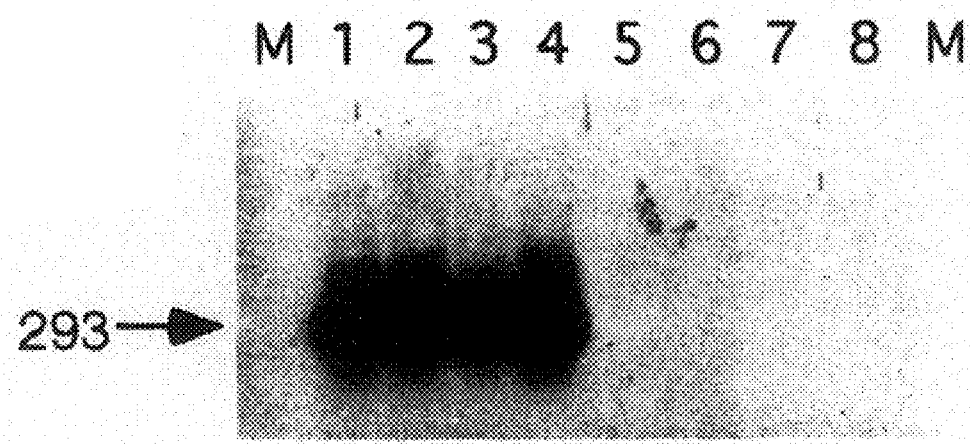
Figure 5A:
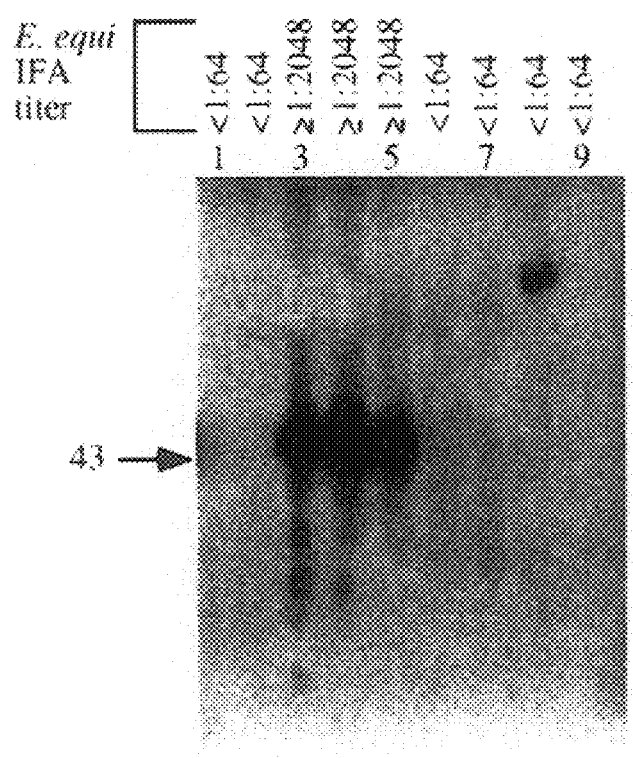

Three Balb/C mice were infected with the HGE agent by syringe inoculation of blood from C.B-17 HGE agent infected mice. Infection ofthe Balb/C mice was confirmed by blood smear and PCR (FIG. 4). HGE seroreactivity was confirmed by testing for *E. equi* antibody by IFA. Consistent with the PCR data, a strong antibody response to the 45 kD fusion protein was detected in all three infected Balb/C mice 28 days after inoculation (FIG. 5A). In contrast, no reactivity was observed in mice infected with *B. burgdorferi* strain N40 or in mice inoculated with blood from uninfected C.B-17 mice.

Figure 5B:
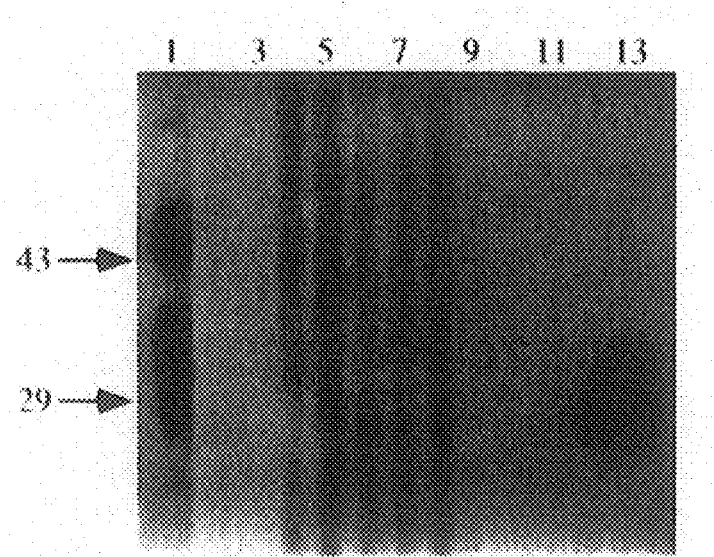

To determine whether the immunoreactivity in infected mice was specific for the ehrlichial portion of the fusion protein, the sera was screened against a GST polypeptide (FIG. 5B). None of the sera reacted with the GST polypeptide under conditions in which the cleaved GST polypeptide was detected by a GST-specific antibody. Thus, the HGE-specific portion of the fusion polypeptide is immunogenic.

Figure 5C:
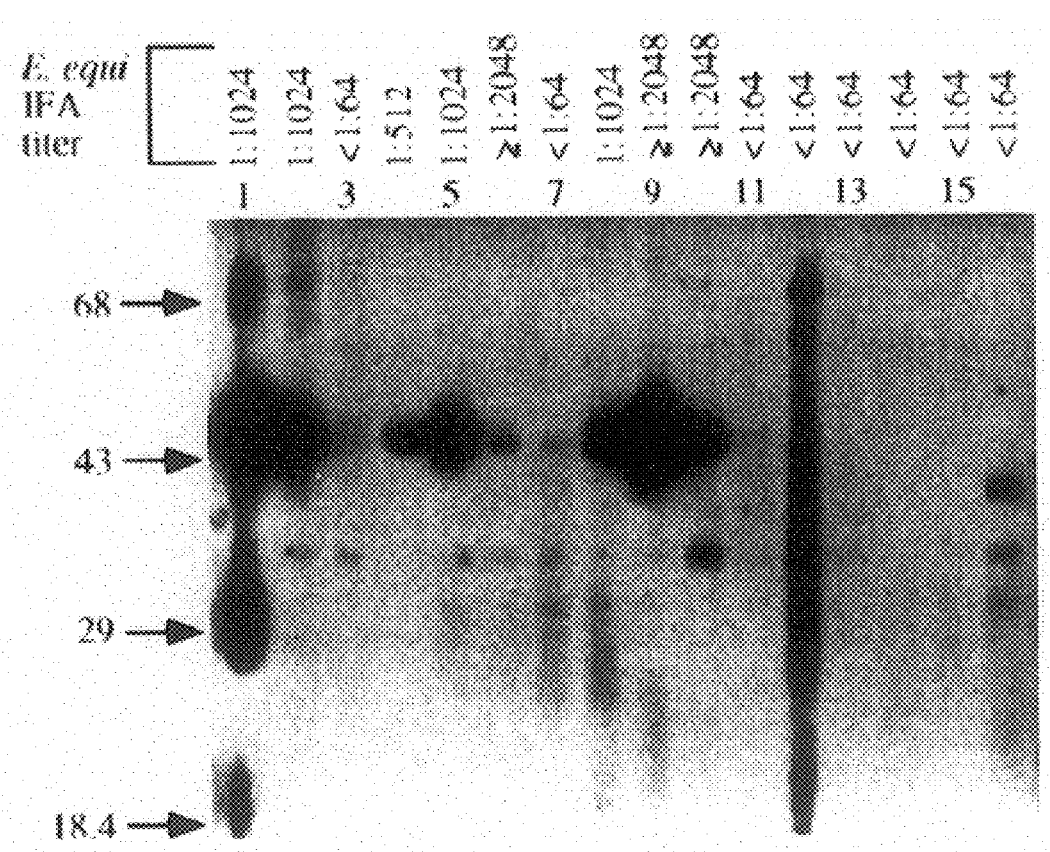

FIG. 5C shows the results from C3H/HeJ mice infected by tick transmission with an east coast strain (NCH-1) of the HGE agent or with *B. burgdorferi* strain N40. The east coast strain of the HGE agent was isolated from a patient from Nantucket Island, Mass. Deer ticks experimentally infected with the NCH-1 strain of the HGE agent were allowed to feed upon nine C3H/HeJ mice as described by Telford et al., *Proc Natl. Acad. Sci. USA*, 93, 6209 (1996). The mice were then followed for up to 19 months by direct smear evaluation and *E. equi* IFA.

Antibody responses to affinity purified ehrlichial HGE agent HSP-60 antigen could also be detected for six or more months after infection. However, the level of reactivity on Western blot correlated qualitatively rather than quantitatively with the IFA titers (FIG. 5C). One mouse, infected for six months, was weakly seroreactive with the fusion polypeptide, yet was IFA negative at a 1:64 screening titer (FIG. 5C, lane 7). This discordance was not observed with any of the other mice, infected or uninfected, and may be due to a cut off titer (1:64) that is too high.

Two C3H/HeJ mice which were fed upon by infected Ixodes sp. ticks were negative by blood smear evaluation.

These mice also had no significant antibody response to *E. equi* antigens, as determined by the E.equi IFA assay, or to the HGE-specific HSP-60 fusion polypeptide (FIG. 5C, lanes 3 and 11). Negative controls included sera from three mice that were fed upon by uninfected ticks and two mice infected with the N40 strain of *B. burgdorferi* by tick inoculation. None of the sera from these negative control animals showed reactivity to the 45 kD fusion polypeptide. However, one serum from a Borrelia infected animal did show background reactivity which may be due to the presence of *E. coli* proteins which co-purified with the fusion polypeptide (lane 16).

Thus, the HSP60-like polypeptide and other immunogenic polypeptides from the agent which is associated with HGE agent can be used as immunodiagnostic reagents for immunodiagnostic testing for infections with this agent. Thus, these reagents may be useful to detect HGE specific infections in humans and other mammals, such as deer.

Moreover, this reagent may also be used to detect monocytic ehrlichiosis due to *E. chaffeensis* infection, in light of the prevalence of *E. chaffeensis* infection and the relatedness of the agent which is associated with HGE to *E. chaffeensis*. Therefore, immunoreactive polypeptides of the invention may comprise genus-specific epitopes, species-specific epitopes, or both.

All cited publication and patents are incorporated by reference herein. The invention is not limited to the exact details shown and described, for it should be understood that many variations and modifications may be made while remaining within the spirit and scope of the invention defined by the claims.

What is claimed is:

1. An isolated and purified immunogenic polypeptide comprising SEQ ID NO:2 which polypetide is associated with granulocytc ehrlichiosis in a mammal, and which polypeptide has an approximate molecular weight of 59 kDa.

2. An isolated and purified immunogenic polypeptide comprising residues 184 to 373 of SEQ ID NO:2.

3. An immunogenic composition comprising a polypeptide comprising SEQ ID NO:2 which polypeptide is associated with granulocytic ehrlichiosis in a mammal, and which polypeptide has an approximate molecular weight of 59 kDa, or comprising a polypeptide comprising residues 184 to 373 of SEQ ID NO:2, in combination with a pharmaceutically acceptable carrier, wherein the administration of the immunogenic composition to a mammal induces the production of antibodies to the polypeptide.

4. A fusion polypeptide comprising a heterologous peptide and an immunogenic polypeptide comprising residues 184 to 373 of SEQ ID NO:2.

* * * * *

UNITED STATES PATENT AND TRADEMARK OFFICE
CERTIFICATE OF CORRECTION

PATENT NO. : 6,403,093 B1
DATED : June 11, 2002
INVENTOR(S) : Persing et al.

It is certified that error appears in the above-identified patent and that said Letters Patent is hereby corrected as shown below:

Column 2,
Line 32, after "amino acid" delete "Li".

Column 10,
Line 64, delete "finction" and insert -- function --, therefor.

Column 11,
Line 6, delete "finction" and insert -- function --, therefor.
Line 8, delete "MRNA" and insert -- mRNA --, therefor.

Column 16,
Line 40, after "patients" delete ",".

Column 17,
Line 25, at the end of "TABLE 2" insert -- [a]Ribosomal RNA gene primers reflect the *E. equi* numbering (M73223).
[b]Heat shock protein gene primers are based on the numbering for the *E. chaffeensis* HSP60 homologue. --.

Column 19,
Line 21, delete "MEGA)" and insert -- (MEGA) --, therefor.
Line 22, delete "istance" and insert -- distance --, therefor.
Line 25, delete "hylogenetic" and insert -- Phylogenetic --, therefor.
Line 52, delete "HGE Agent" and insert -- HGE-Agent --, therefor.
Line 66, delete "HindII" and insert -- HindIII --, therefor.

Column 20,
Line 7, after "DH5" insert -- $\alpha$ --.
Line 12, delete "fuision" and insert -- fusion --, therefor.
Line 62, delete "ofthe" and insert -- of the --, therefor.

Column 21,
Line 18, after "*Proc*" insert -- . --.

UNITED STATES PATENT AND TRADEMARK OFFICE
CERTIFICATE OF CORRECTION

PATENT NO. : 6,403,093 B1
DATED : June 11, 2002
INVENTOR(S) : Persing et al.

It is certified that error appears in the above-identified patent and that said Letters Patent is hereby corrected as shown below:

Column 45,
Line 4, delete "granulocytc" and insert -- granulocytic --, therefor.

Signed and Sealed this

Twenty-first Day of January, 2003

JAMES E. ROGAN
*Director of the United States Patent and Trademark Office*

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 1777 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
CAGTGGGCTG GTAATGAAAT AGAGTTCGAC GGTAAGAAGT TCATAGTGAT GAAGGAGAGT        60

GACATAATAG CTAAGGAAGC ATAGTCTTAT GCTACGGTTG TTTGTTCTAT TGGTCTAAAG       120

TTTAGGAGGT TCAAAAATGT CAAATACGGT AGTCACGGGT GAGGTATTAG ATAAGTCTAT       180

TAGGGAGGTA GTACGCATCC TAGAAGATGC AGTTGGTTGT ACTGCTGGTC CTAAAGGCCT       240

CACTGTAGCG ATTAGTAAGC CTTATGGGTC GCCAGAGATC ACAAAGGATG GCTACAAGGT       300
```

-continued

```
AATGAAGAGT ATAAAGCCTG AAGAACCACT GGCTGCCGCT ATAGCGAGCA TCATTACTCA    360

GAGTGCTTCT CAGTGTAATG ATAAGGTGGG AGATGGAACT ACTACATGCT CCATACTAAC    420

GGCAAAAGTG ATTGAAGAAG TCTCAAAAGC GAAAGCTGCT GGATCTGATA TTGTTAGCAT    480

AAAGAATGG ATTCTCAAGG CTAAGGAAGC GGTTCTTACA GCGCTTATGT CTATGAGACG     540

TGAAGTAGAA GAAGACGAAA TTGCACAAGT TGCAACATTG TCTGCGAATG GAGACAAGAA    600

CATAGGAAGT AAGATTGCAC AGTGTGTTAA AGAAGTCGGT AAAGACGGTG TTATAACTGT    660

TGAAGAAAGC AAAGGCTTCA AGGATCTAGA AGTTGAAAAG ACTGATGGTA TGCAGTTTGA    720

TCGCGGATAT CTTTCGCCTT ACTTTGTTAC AAATGCTGAA AAAATGCTGG TGGAATTTGA    780

AAATCCATAC ATATTCCTTA CTGAAAAGAA GATTAATCTT GTACAAAGCA TTCTACCAAT    840

CTTAGAAAAC GTTGCACGGT CTGGAAGACC ATTGCTCATC ATAGCTGAAG ACGTTGAAGG    900

TGAAGCTCTG AGCACGCTTG TACTCAATAA GCTCCGTGGT GGCCTTCAAG TTGCTGCTGT    960

AAAGGCGCCT GGTTTCGGTG ACAGAAGAAA AGACATGCTT GGCGATATTG CTGTAATAGT   1020

AGGCGCTAAG TATGTAGTAA ATGACGAGCT TGCTGTTAAG ATGGAAGACA TCGCTCTAAG   1080

CGATCTTGGT ACTGCTAAGA GCGTGCGAAT CACAAAAGAC GCAACTACTA TTATAGGTAG   1140

TGTTGATAGC AGTTCTGAAA GCATAGCTAG CAGGACTAAT CAAATCAAAG CTCAGATAGA   1200

AAATTCTAGT TCTGATTATG ACAAGGAAAA GCTTAGAGAA CGTTTAGCGA AGCTTTCCGG   1260

TGGCGTTGCT GTACTCAAGG TTGGTGGATC CAGCGAAGTT GAGGTGAAGG AACGCAAAGA   1320

CAGAGTAGAA GATGCTTTAC ATGCTACTAG AGCTGCTGTT GAGGAAGGTG TAGTACCTGG   1380

TGGTGGGGCT GCATTGCTTT ATGCGCTTTC GTCTCTAGAC GGTCTAAAAG CAAGAATGA    1440

CGACGAACAA TGGGGTATAG ACATTATACG TCGCGCTGCT TGTGCTCCAA TCAAAAGAAT   1500

CATCAAGAAT TCTGGTTCTG AAGAAGCACC ATGCGTAATT CAACACTTGT TGAAGCAAAA   1560

CGACAAGGAA CTTATCTACA ATGTGGATAC TATGAACTAC GCGAATGCTT TTACATCTGG   1620

AGTTATGGAT CCTCTCAAAG TAGTACGTAT CGCGTTTGAT TTAGCTGTAT CACTCGCTGC   1680

AGTATTCATG ACTTTGAATG CAGTGGTTGT TGATGTTCCT AGTAAGAACG ACGCTGCTGG   1740

TGCTGGCGCT GGTGGTATGG GAGGCATGGG TGGTATG                           1777
```

(2) INFORMATION FOR SEQ ID NO:2:

(i) SEQUENCE CHARACTERISTICS:
        (A) LENGTH: 541 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Asn Thr Val Val Thr Gly Glu Val Leu Asp Lys Ser Ile Arg
 1               5                  10                  15

Glu Val Val Arg Ile Leu Glu Asp Ala Val Gly Cys Thr Ala Gly Pro
            20                  25                  30

Lys Gly Leu Thr Val Ala Ile Ser Lys Pro Tyr Gly Ser Pro Glu Ile
        35                  40                  45

Thr Lys Asp Gly Tyr Lys Val Met Lys Ser Ile Lys Pro Glu Glu Pro
    50                  55                  60

Leu Ala Ala Ala Ile Ala Ser Ile Ile Thr Gln Ser Ala Ser Gln Cys
65                  70                  75                  80
```

```
Asn Asp Lys Val Gly Asp Gly Thr Thr Thr Cys Ser Ile Leu Thr Ala
                85                  90                  95

Lys Val Ile Glu Glu Val Ser Lys Ala Lys Ala Gly Ser Asp Ile
            100                 105                 110

Val Ser Ile Lys Asn Gly Ile Leu Lys Ala Lys Glu Ala Val Leu Thr
        115                 120                 125

Ala Leu Met Ser Met Arg Arg Glu Val Glu Asp Glu Ile Ala Gln
    130                 135                 140

Val Ala Thr Leu Ser Ala Asn Gly Asp Lys Asn Ile Gly Ser Lys Ile
145                 150                 155                 160

Ala Gln Cys Val Lys Glu Val Gly Lys Asp Gly Val Ile Thr Val Glu
            165                 170                 175

Glu Ser Lys Gly Phe Lys Asp Leu Glu Val Glu Lys Thr Asp Gly Met
            180                 185                 190

Gln Phe Asp Arg Gly Tyr Leu Ser Pro Tyr Phe Val Thr Asn Ala Glu
        195                 200                 205

Lys Met Leu Val Glu Phe Glu Asn Pro Tyr Ile Phe Leu Thr Glu Lys
    210                 215                 220

Lys Ile Asn Leu Val Gln Ser Ile Leu Pro Ile Leu Glu Asn Val Ala
225                 230                 235                 240

Arg Ser Gly Arg Pro Leu Leu Ile Ile Ala Glu Asp Val Glu Gly Glu
            245                 250                 255

Ala Leu Ser Thr Leu Val Leu Asn Lys Leu Arg Gly Gly Leu Gln Val
            260                 265                 270

Ala Ala Val Lys Ala Pro Gly Phe Gly Asp Arg Arg Lys Asp Met Leu
        275                 280                 285

Gly Asp Ile Ala Val Ile Val Gly Ala Lys Tyr Val Val Asn Asp Glu
    290                 295                 300

Leu Ala Val Lys Met Glu Asp Ile Ala Leu Ser Asp Leu Gly Thr Ala
305                 310                 315                 320

Lys Ser Val Arg Ile Thr Lys Asp Ala Thr Thr Ile Ile Gly Ser Val
            325                 330                 335

Asp Ser Ser Ser Glu Ser Ile Ala Ser Arg Thr Asn Gln Ile Lys Ala
            340                 345                 350

Gln Ile Glu Asn Ser Ser Asp Tyr Asp Lys Glu Lys Leu Arg Glu
        355                 360                 365

Arg Leu Ala Lys Leu Ser Gly Gly Val Ala Val Leu Lys Val Gly Gly
    370                 375                 380

Ser Ser Glu Val Glu Val Lys Glu Arg Lys Asp Arg Val Glu Asp Ala
385                 390                 395                 400

Leu His Ala Thr Arg Ala Ala Val Glu Glu Gly Val Val Pro Gly Gly
            405                 410                 415

Gly Ala Ala Leu Leu Tyr Ala Leu Ser Ser Leu Asp Gly Leu Lys Gly
            420                 425                 430

Lys Asn Asp Asp Glu Gln Trp Gly Ile Asp Ile Ile Arg Arg Ala Ala
        435                 440                 445

Cys Ala Pro Ile Lys Arg Ile Ile Lys Asn Ser Gly Ser Glu Glu Ala
    450                 455                 460

Pro Cys Val Ile Gln His Leu Leu Lys Gln Asn Asp Lys Glu Leu Ile
465                 470                 475                 480

Tyr Asn Val Asp Thr Met Asn Tyr Ala Asn Ala Phe Thr Ser Gly Val
            485                 490                 495

Met Asp Pro Leu Lys Val Val Arg Ile Ala Phe Asp Leu Ala Val Ser
```

```
                    500                 505                 510
Leu Ala Ala Val Phe Met Thr Leu Asn Ala Val Val Asp Val Pro
                515                 520                 525
Ser Lys Asn Asp Ala Ala Gly Ala Gly Ala Gly Gly Met
530                 535                 540
```

(2) INFORMATION FOR SEQ ID NO:3:

(i) SEQUENCE CHARACTERISTICS:
        (A) LENGTH: 549 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ala Asn Val Val Thr Gly Glu Gln Leu Asp Lys Ser Ile Arg
 1               5                  10                  15
Glu Val Val Arg Ile Leu Glu Asp Ala Val Gly Cys Thr Ala Gly Pro
                20                  25                  30
Lys Gly Leu Thr Val Ala Ile Gly Lys Ser Tyr Gly Ala Pro Glu Val
                35                  40                  45
Thr Lys Asp Gly Tyr Lys Val Ile Lys Ser Ile Lys Pro Glu Asp Pro
 50                  55                  60
Leu Ala Leu Ala Ile Ala Asn Ile Ile Thr Gln Ser Ala Ser Gln Cys
65                   70                  75                  80
Asn Asp Lys Val Gly Asp Gly Thr Thr Thr Cys Ser Ile Leu Thr Ala
                85                  90                  95
Lys Val Ile Glu Glu Val Ser Lys Ala Lys Ala Ala Gly Ala Asp Ile
                100                 105                 110
Val Cys Ile Lys Glu Gly Val Leu Lys Ala Lys Glu Ala Val Leu Glu
                115                 120                 125
Ala Leu Met Ser Met Lys Arg Glu Val Leu Ser Glu Glu Ile Ala
                130                 135                 140
Gln Val Ala Thr Ile Ser Ala Asn Gly Asp Lys Asn Ile Gly Ser Lys
145                 150                 155                 160
Ile Ala Gln Cys Val Gln Glu Val Gly Lys Asp Gly Val Ile Thr Val
                165                 170                 175
Glu Glu Ser Lys Gly Phe Lys Glu Leu Asp Val Glu Lys Thr Asp Gly
                180                 185                 190
Met Gln Phe Asp Arg Gly Tyr Leu Ser Pro Tyr Phe Val Thr Asn Ser
                195                 200                 205
Glu Lys Met Leu Val Glu Phe Glu Asn Pro Tyr Ile Leu Leu Thr Glu
                210                 215                 220
Lys Lys Leu Asn Ile Ile Gln Pro Ile Leu Pro Ile Leu Glu Asn Val
225                 230                 235                 240
Ala Arg Ser Gly Arg Pro Leu Leu Ile Ile Ala Glu Asp Val Glu Gly
                245                 250                 255
Glu Ala Leu Ser Thr Leu Val Leu Asn Lys Leu Arg Gly Gly Leu His
                260                 265                 270
Val Ala Ala Val Lys Ala Pro Gly Phe Gly Asp Arg Arg Lys Asp Met
                275                 280                 285
Leu Gly Asp Ile Ala Ile Leu Thr Gly Ala Lys His Val Ile Ser Asp
                290                 295                 300
Asp Leu Ala Ile Lys Met Glu Asp Leu Thr Leu Ala Glu Leu Gly Thr
```

```
305                 310                 315                 320
Ala Lys Asn Ile Arg Ile Thr Lys Asp Thr Thr Ile Ile Gly Ser
                325                 330                 335

Val Asp Asn Ser Ser Ala Asn Val Gln Ser Arg Ile Asn Gln Ile Lys
                340                 345                 350

Met Gln Ile Glu Ala Ser Thr Ser Asp Tyr Asp Lys Glu Lys Leu Arg
                355                 360                 365

Glu Arg Leu Ala Lys Leu Ser Gly Val Ala Val Leu Lys Val Gly
    370                 375                 380

Gly Ser Ser Glu Val Glu Val Lys Glu Arg Lys Asp Arg Val Glu Asp
385                 390                 395                 400

Ala Leu His Ala Thr Arg Ala Ala Val Glu Glu Gly Val Val Pro Gly
                405                 410                 415

Gly Gly Ala Ala Leu Leu Tyr Thr Leu Ser Val Leu Glu Asn Leu Lys
                420                 425                 430

Ser Lys Asn Asp Asp Glu Gln Leu Gly Ile Asn Ile Val Lys Arg Ala
                435                 440                 445

Leu Gln Ala Pro Ile Lys Arg Ile Ile Lys Asn Ser Gly Ser Glu Asn
    450                 455                 460

Ala Pro Cys Val Ile Ala His Leu Leu Lys Gln Asn Asp Lys Glu Leu
465                 470                 475                 480

Ile Phe Asn Val Asp Thr Met Asn Phe Ala Asn Ala Phe Thr Ser Gly
                485                 490                 495

Val Ile Asp Pro Leu Lys Val Val Arg Ile Ala Phe Asp Phe Ala Val
                500                 505                 510

Ser Leu Ala Ala Val Phe Met Thr Leu Asn Ala Ile Val Val Asp Val
    515                 520                 525

Pro Ser Lys Asp Asp Ala Asn Ala Gly Ala Gly Met Gly Gly Met
    530                 535                 540

Gly Gly Met Gly Gly
545

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GAAGAAATTG CHCAAGTWGC                                                     20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:5:

TTCTTCAACA GCWGCTCTAG                                                    20

(2) INFORMATION FOR SEQ ID NO:6:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CGYCAGTGGG CTGGTAATGA A                                                  21

(2) INFORMATION FOR SEQ ID NO:7:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:7:

CCATACCWCC CATGCCTC                                                      18

(2) INFORMATION FOR SEQ ID NO:8:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

YGGATAYCTT TCKCCTTAYT TT                                22

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

CTTGGTACTG CTAAGAGCGT G                                 21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

CCTTCCTCAA CAGCAGCTCT A                                 21

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GCAAGCTTAA GACATGCAAG TC                                22

(2) INFORMATION FOR SEQ ID NO:12:

(i) SEQUENCE CHARACTERISTICS:
        (A) LENGTH: 19 base pairs
        (B) TYPE: nucleic acid

```
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:12:

CCAGGTATAG ATCATCGCC                                                    19

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:13:

CAAACAACCG TAGCATAAGA CTAT                                              24

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

AAATCAATTA GAGAAGTTGT                                                   20

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:
```

(vi) ORIGINAL SOURCE:

(xi) SEQUENCE DESCRIPTION: SEQ ID NO:15:

TAGGACCAGC AGTACAACCA ACTGCAT                                27

(2) INFORMATION FOR SEQ ID NO:16:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

TACTCAGAGT GCTTCTCAGT GTAATGA                                27

(2) INFORMATION FOR SEQ ID NO:17:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:17:

CAATATCAGA TCCAGCAGCT T                                      21

(2) INFORMATION FOR SEQ ID NO:18:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

AAGACGGTGT TATAACTGTT GAAG                                   24

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:19:

AAKCCTTTRC TTTCTTCAAC                                               20

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

TGCTGGTGGA ATTTGAAAAT C                                             21

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

GTGACAGAAG AAAAGACATG CT                                            22

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

GATATTGCTG TAATAGTAGG CGCTA                                              25

(2) INFORMATION FOR SEQ ID NO:23:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:23:

CTTTTGTGAT TCGCACGCTC T                                                  21

(2) INFORMATION FOR SEQ ID NO:24:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

TGGCGTTGCT GTACTCAAGG T                                                  21

(2) INFORMATION FOR SEQ ID NO:25:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:25:

CATCTTCTAC TCTGTCTTTG CGT                                                23

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:26:

TCAACAGCAG CTCTAGTTGC                                               20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:27:

CTAGAGCTGC TGTTGAAGAA                                               20

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:28:

ACCAGGTACT ACACCTTCCT CAA                                           23